US00PP20621P2

(12) United States Plant Patent
Evers

(10) Patent No.: US PP20,621 P2
(45) Date of Patent: Dec. 29, 2009

(54) FLORIBUNDA ROSE PLANT HAVING LARGE FLOWERS AND NAMED 'TAN01360'

(50) Latin Name: *Rosa hybrida*
Varietal Denomination: TAN01360

(75) Inventor: Christian Evers, Uetersen (DE)

(73) Assignee: Rosen Tantau Mathias Tantau Nachfolger, Uetersen (DE)

( * ) Notice: Subject to any disclaimer, the term of this patent is extended or adjusted under 35 U.S.C. 154(b) by 0 days.

(21) Appl. No.: 12/001,926

(22) Filed: Dec. 12, 2007

(51) Int. Cl.
*A01H 5/00* (2006.01)

(52) U.S. Cl. ..... Plt./150
(58) Field of Classification Search ..... Plt./150, Plt./139
See application file for complete search history.

(56) References Cited

OTHER PUBLICATIONS

Letter.

*Primary Examiner*—Kent L Bell
(74) *Attorney, Agent, or Firm*—Klarquist Sparkman, LLP

(57) ABSTRACT

Floribunda rose plant having large ball shaped, bright red flowers and healthy foliage.

1 Drawing Sheet

Genus and species: *Rosa hybrida.*
Variety denomination: 'TAN01360'.

ORIGIN OF THE INVENTION

The present invention relates to a new and distinct variety of a large-flowered floribunda rose plant named 'TAN01360' which was originated by me by crossing the variety 'RT98097' (seed parent), with the variety 'Mein München' (pollen parent).

BACKGROUND OF THE INVENTION

The primary objective of this breeding was to produce a new floribunda rose variety having large, ball shaped, bright red flowers and healthy foliage.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Very nice ball shaped flowers.
2. Bright red flower.
3. Healthy foliage.

This new variety is a good garden rose variety for private gardens, parks and landscaping.

Asexual reproduction of this new variety by grafting, as performed at Uetersen, Germany, shows that the foregoing characteristics and distinctions come true to form and are established and transmitted through succeeding propagations.

Comparison with Parents

The new variety 'TAN01360' differs from the seed parent, RT98097, in classification, ('TAN01360' is classified as a floribunda grandiflora (nostalgic hybrid tea) while RT98097 is classified as a hybrid tea). The pollen parent has a yellow-orange flower color.

Comparison with Similar Variety

'TAN01360' differs from 'Meiangle' in plant height (60–80 cm tall for 'TAN01360' versus 40–60 cm tall for 'Meiangele').

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—'RT98097' hybrid tea red.
*Pollen parent.*—'Mein München'.

FLOWER

Observations made Nov. 2, 2007, from plants that were three years in age, growing in a garden environment at Uetersen, Germany.

Blooming habit: Continuous.

Bud:

*Size.*—About 3.1 cm long and 4 cm in diameter when the petals start to unfurl.
*Form.*—The bud form is globular.

*Color.*—When sepals first divide, bud color is Red (RHS 46A). When half blown, the upper sides of the petals are Red (RHS 46B). The lower sides of the petals are Red (RHS 46D).

*Sepals.*—Color: Upper surface: Red (RHS 46D). Lower surface: Red (RHS 46A). Length: 3.8 cm. Width: 4.0 cm. Shape: Circular. Surface: Smooth. There are three lightly appendaged sepals. There are five unappendaged sepals with smooth edges.

*Receptacle.*—Color: Green (RHS 144A). Shape: Pear. Size: Broad, about 1.3 cm long × 1.0 cm in width. Surface: Smooth.

*Peduncle.*—Length: Averaging about 4.8 cm. Diameter: 0.3 cm. Surface: Smooth. Color: Green (RHS 146D). Strength: Erect.

Bloom:

*Size.*—Large. Average open diameter is about 5.8 cm.

*Borne.*—In clusters of 3–4 blooms having a rounded shape.

*Stems.*—Strength: Normal. Average length is about 45 cm with a diameter of 0.3 cm. Color of younger stems: Green (RHS 141 B). Color of older (woody) stems is Brown (RHS 152A).

*Form.*—When first open: Globular, retains its form to the end.

*Petalage.*—Number of petals under normal conditions: 91 (very double).

*Color.*—The upper sides of the petals are Red (RHS 53D). The reverse sides of the petals are Red (RHS 53B). The base of the petals has a little bright spot, Red (RHS 36D). The major color on the upper sides is Red (RHS 46D).

*Variegations.*—None.

*Fragrance.*—None.

Petals:

*Thickness.*—Thin.

*Size.*—About 3.6 cm in width × 4.9 cm long.

*Surface texture.*—Smooth.

*Shape.*—Round.

*Margin.*—Smooth.

*Apex shape.*—Rounded.

*Base shape.*—Rounded.

*Form.*—Edges slightly quilled.

*Arrangement.*—Irregular.

*Petaloids.*—Number: 16. Color: Same as petals.

*Persistence.*—Petals drop off cleanly before drying.

*Lastingness.*—On the plant: Long (about 16 days). As a cut flower: Fair (about 10 days).

Reproductive parts:

*Stamens.*—Number: No stamens visible, probably most stamens turned to petals.

*Pistils.*—Number: 33. Length: 0.6 cm.

*Styles.*—Color: Orange-Red (RHS 25A). Length: 0.5 cm.

*Stigmas.*—Color: Yellow. Length: 0.1 cm.

*Hips.*—No hips produced.

PLANT

*Form.*—Bush.

*Growth.*—Medium.

*Age to maturity.*—Five years.

*Mature plant.*—Height: 60–80 cm. Width: 50 cm.

*Rootstock.*—*Rosa canina* 'Inermis'.

Foliage: Number of leaflets on normal mid-stem leaves: 7.

*Size.*—Medium. About 12 cm long × 8.1 cm wide.

*Quantity.*—Normal.

*Color.*—New foliage: Upper side: Green (RHS 141A). Lower side: Green (RHS 137D). Old foliage: Upper side: Green (RHS 141A). Lower side: Green (RHS 137D).

Leaflets:

*Size.*—About 5.4 cm long × 3.5 cm wide.

*Shape.*—Pointed.

*Base shape.*—Oval.

*Apex shape.*—Pointed.

*Texture.*—Leathery.

*Edge.*—Serrated.

*Serrations.*—Single.

*Petiole.*—Color: Green (RHS 137D).

*Petiole rachis.*—Color: Green (RHS 137C). Underside: With prickles about 0.2 cm.

*Auricles.*—Shape: Pointed.

*Stipules.*—Length: 0.8 cm, serrated.

*Disease resistance.*—Resistant to rust, mildew and blackspot under normal growing conditions. Very good resistance to fungal diseases.

*Vein color.*—Green (RHS 139D).

*Venation pattern.*—Pyramidal.

Wood:

*New wood.*—Color: Green (RHS 146A). Bark: Smooth.

*Old wood.*—Color: Brown (RHS 174A). Bark: Rough.

Prickles:

*Quantity.*—Ordinary, on main canes from base: 24 per 15 cm of wood.

*Form.*—Hooked downward.

*Length.*—0.9 cm.

*Color when young.*—Brown (RHS 174B).

*Color when mature.*—Brown (RHS 174B).

Small prickles:

*Quantity.*—On main stalks: Few.

*Color.*—Green (RHS 137A), when young; Brown (RHS 174A), when mature.

Winter hardiness: Hardy to Zone 6.

I claim:

1. A new and distinct variety of floribunda rose plant, substantially as herein shown and described, characterized particularly by large ball shaped, bright red flowers and healthy foliage.

* * * * *

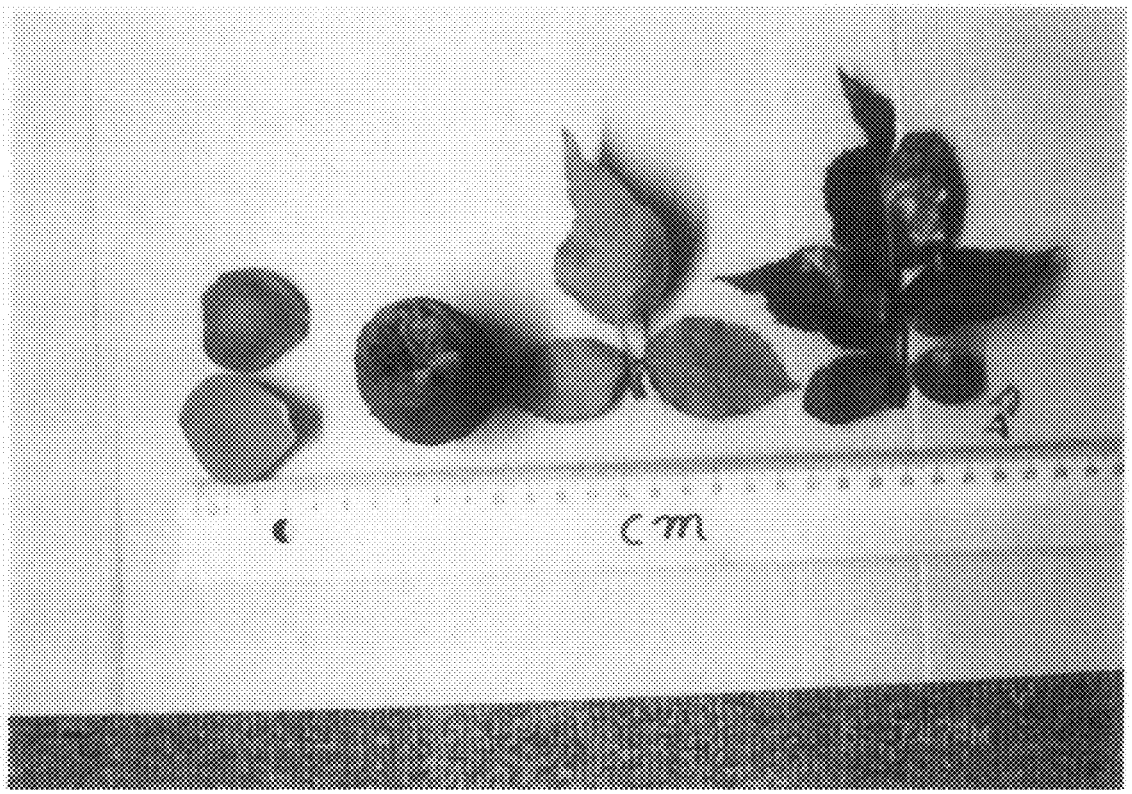
cm
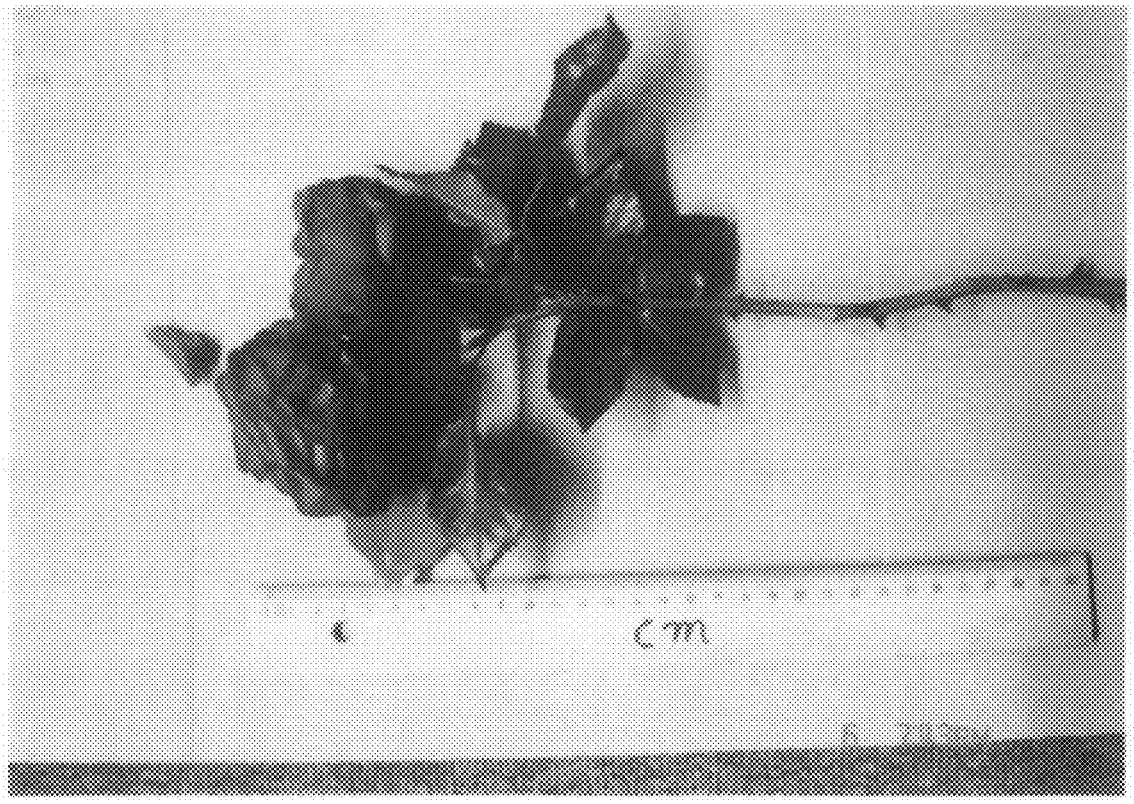
cm